US006500141B1

(12) United States Patent
Irion et al.

(10) Patent No.: US 6,500,141 B1
(45) Date of Patent: Dec. 31, 2002

(54) APPARATUS AND METHOD FOR TREATING BODY TISSUE, IN PARTICULAR SOFT SURFACE TISSUE WITH ULTRASOUND

(75) Inventors: Klaus M. Irion, Liptingen (DE); Nicanor G. Isse, Burbank, CA (US)

(73) Assignee: Karl Storz GmbH & Co. KG (DE)

( * ) Notice: Subject to any disclaimer, the term of this patent is extended or adjusted under 35 U.S.C. 154(b) by 167 days.

(21) Appl. No.: 09/612,124

(22) Filed: Jul. 7, 2000

Related U.S. Application Data

(63) Continuation of application No. PCT/EP99/00074, filed on Jan. 8, 1999.

(30) Foreign Application Priority Data

Jan. 8, 1998 (DE) .......................................... 198 00 416

(51) Int. Cl.[7] .............................................. A61B 17/20
(52) U.S. Cl. ...................... 604/22; 604/20; 604/890.1; 604/290; 601/2
(58) Field of Search .............................. 604/22, 19, 20, 604/290, 289, 310, 118, 131, 890.1; 607/1, 2, 3, 61, 72; 601/2, 3; 606/169

(56) References Cited

U.S. PATENT DOCUMENTS

| | | | | |
|---|---|---|---|---|
| 4,958,626 A | * | 9/1990 | Nambu et al. .................. 601/3 |
| 5,139,496 A | | 8/1992 | Hed .............................. 606/23 |
| 5,590,653 A | * | 1/1997 | Aida et al. ..................... 601/3 |
| 5,601,526 A | | 2/1997 | Chapelon et al. ............... 601/3 |
| 5,618,275 A | | 4/1997 | Bock ........................... 604/290 |
| 5,665,053 A | * | 9/1997 | Jacobs ........................... 601/2 |
| 5,853,005 A | * | 12/1998 | Scanlon ......................... 601/2 |
| 5,983,131 A | * | 11/1999 | Weaver et al. ................ 604/20 |
| 6,009,343 A | * | 12/1999 | Shain et al. ................... 604/20 |
| 6,039,048 A | * | 3/2000 | Silberg ......................... 604/22 |
| 6,096,000 A | * | 8/2000 | Tachibana et al. ............. 604/20 |
| 6,183,434 B1 | * | 2/2001 | Eppstein ....................... 604/22 |
| 6,234,990 B1 | * | 5/2001 | Rowe et al. ................... 604/22 |
| 6,341,232 B1 | * | 1/2002 | Conn et al. .................... 604/20 |

FOREIGN PATENT DOCUMENTS

| | | |
|---|---|---|
| DE | 198 00 416 A1 | 7/1999 |
| EP | 0 459 239 A2 | 5/1991 |
| EP | 0 614 651 A1 | 3/1994 |
| EP | 0 668 052 A2 | 2/1995 |

* cited by examiner

Primary Examiner—Teresa Walberg
Assistant Examiner—Fadi H. Dahbour
(74) Attorney, Agent, or Firm—St. Onge Steward Johnston & Reens LLC

(57) ABSTRACT

An apparatus for treating body tissue, in particular superficial soft tissue, with ultrasound, comprises an ultrasonic generation unit and an applicator, by means of which the ultrasound can be irradiated from an applicator surface facing the body surface from outside through the body surface into the body tissue. A suction apparatus for sucking in the body surface against the applicator surface is provided.

70 Claims, 3 Drawing Sheets

APPARATUS AND METHOD FOR TREATING BODY TISSUE, IN PARTICULAR SOFT SURFACE TISSUE WITH ULTRASOUND

CROSS REFERENCE TO PENDING APPLICATION

This is a continuation of pending International Application PCT/EP99/00074.

BACKGROUND OF THE INVENTION

The invention relates to an apparatus for treating body tissue, particularly soft surface tissue, with ultrasound. The apparatus comprises an ultrasound generation unit and an applicator with which ultrasound can be emitted from an applicator surface facing the body surface from the outside through the body surface into the body tissue.

The invention further relates to a method for treating body tissue, in particular soft surface tissue, with ultrasound. An apparatus as mentioned at the outset is known from the U.S. company brochure of Wells Johnson Company, Tucson, Ariz., U.S.A, entitled "Introducing SILBERG E.U.S.™ External Ultrasonic System".

The use of ultrasound for healing purposes has increased in importance. Depending on the therapy, ultrasound is applied in the form of continuous or pulsed ultrasound wave fields.

Ultrasound has been successfully employed in so-called exterior shock wave therapy as well as ultrasound wave therapy for treating stones in the kidneys, urethra, gall and the like. An apparatus for treating body stones, a so-called lithotriptor, is known for example from the Swiss company brochure of Storz Medical AG, Kreuzlingen, Switzerland, entitled "STORZ MODULITH®-Systeme für die extrakorporale Lithotripsie". Short ultrasound pulses generated with this lithotriptor externally, i.e. outside of the body, are coupled into the body and focused on the stones in the body. The stones are localized beforehand by ultrasound imaging devices or X-ray systems.

Developments are being made in the external treatment of tumors in which special ultrasound applicators generate ultrasound waves which are transmitted to the tumor from the outside. By special control of the time the ultrasound acts on the tumor, an overheating of the tumorous tissue results and leads to its destruction.

It is not only the thermal effect of ultrasound which leads to dissolution of the cell structure, but also the pure mechanical effect in the form of cavitation. Sound waves propagate in a medium in the form of periodically varying density fluctuations of the medium. A volume element of the medium is alternately compressed (higher pressure) and expanded (lower pressure). The lower pressure can lead to vapor bubble formation in the fluid, for example in cell fluid, where in the end, the cell walls and/or the cell structure is destroyed.

It has been shown that this effect of ultrasound is suitable for disintegration or dissolution of soft tissue, for example fat tissue. The apparatus disclosed in the above-mentioned U.S. company brochure is employed for removing fat tissue close to the surface. The known apparatus comprises an applicator with which ultrasound is coupled from the outside through the body surface into the lower lying soft tissue.

A drawback of the known apparatus is the difficulty in achieving a uniform coupling of the applicator over its entire active surface to the tissue to be treated. When this is not the case, not only is the applied ultrasound energy not optimally utilized, an increased heat development also occurs.

A further drawback of the known apparatus is that it is not possible to control the depth effect of ultrasound, i.e. The penetration depth of the active ultrasound or its focus. When applying the applicator, a compression or a displacement of the underlying tissue can result, such that the individual tissue layers no longer have their original thickness or disposition. Without depth control, it is not possible to couple the ultrasound properly to the body tissue to be treated. There is also the danger that tissue which is not to be treated could be damaged.

Another apparatus of the present type for treating body tissue with ultrasound is disclosed in U.S. Pat. No. 5,618,275. The apparatus comprises an applicator having a housing in which an ultrasound transducer is embedded. A collar is provided on the housing on the side facing the body surface, which together with the housing forms a chamber of predetermined volume. A substance to be applied to the body surface is held in the chamber between the body surface and the applicator surface, such that the substance cannot be released from the chamber formed by the collar. The collar is formed of rubber or the like to be flexible. The therapeutic substance held by the collar between the applicator surface and the body surface more easily penetrates the tissue by means of the ultrasound treatment.

An object of the present invention is to provide an improved apparatus of the above-mentioned type, where ultrasound can be specifically coupled to the body tissue to be treated and where depth control of the ultrasound therapy can be achieved.

SUMMARY OF THE INVENTION

According to the present invention, an apparatus for treating body tissue, in particular superficial soft tissue, with ultrasound, is provided, comprising: an ultrasonic generation unit; an applicator having an applicator surface facing the body surface from which said ultrasound can be irradiated through said body surface into said body tissue, wherein a suction apparatus is provided for taking in said body surface against said applicator surface.

The present invention further provides a method for treating body tissue, in particular superficial soft tissue, with ultrasound, comprising the steps of: providing an ultrasonic generation unit and an applicator having an applicator surface; taking in said body surface against said applicator surface and irradiating said ultrasound from said applicator surface from outside through a body surface into said body tissue.

By taking in the body surface against the applicator surface, the underlying body tissue is drawn against the applicator, whereby a fixation of the tissue to the applicator is achieved. Through this fixation, the ultrasound can be optimally coupled into the tissue over its surface for the purposes of therapy. The treatment region in the body in terms of distance is fixed by sucking in the tissue. Thus ultrasound can be specifically applied to the body tissue in controlled manner because the distance between the emission point of ultrasound from the applicator and the body tissue is defined.

A sucking in of the body surface and thus the underlying tissue to be treated has the advantage over pressing the applicator onto the body surface in that the soft tissue underlying the surface is not displaced laterally or pushed outwardly. Thus the amount of soft tissue in the region of the applicator is not reduced, but on the contrary, it is drawn into the coupling region of the ultrasound.

In a preferred embodiment of the present invention, the suction apparatus is formed as a suction cup.

This can be realized by providing the applicator with at least one suction cup or forming the applicator itself as a suction cup in order to fix the tissue to the applicator. An embodiment of the applicator formed as a suction cup can be achieved by providing a lip structure at the edge of the applicator, which is flexible and elastic. When pressing the applicator onto the body surface, the lips produce a corresponding counter-force, whereby the body surface is drawn onto the applicator surface. Further, the lips must be configured such that they form a seal with the body surface either alone or together with a sealing substance, whereby the applicator itself should also be sealed.

In a further preferred embodiment, the applicator comprises at least one suction channel opening into the applicator surface, which is connected to an external suction device.

With this measure, a vacuum can be easily generated between the body surface and the applicator surface. A vacuum pressure is applied by the external suction apparatus to the suction channel joining into the applicator surface, whereby the body surface is sucked onto the applicator surface. The suction of the body surface can be further improved by providing a plurality of suction channels joining into the applicator surface. If only one suction channel is provided, it is advantageous to provide it approximately at the center of the applicator surface. The suction channel can also be connected to one or more open channels or grooves in the surface of the applicator.

In another preferred embodiment of the present invention, the ultrasound can be coupled into the body tissue by the applicator in a focused manner. By focused introduction of ultrasound into the body tissue, the ultrasound can be concentrated in a small volume element of only a few millimeters. The density of the focused ultrasound is increased by the concentration whereby the therapeutic effect is improved, namely the disintegration of the soft tissue. In addition, this allows one to work with a reduced energy density of the ultrasound, which leads to the further advantage that the energy density at the body surface is reduced and an extensive heating of the dermis is avoided. A focused introduction of ultrasound into body tissue is not possible in the apparatus mentioned above disclosed in the U.S. company brochure.

A focusing possibility exists, which is largely independent of the applicator surface, for example by the time dependence in driving the individual transducer elements of the applicator (phased array technique).

In a further preferred embodiment, the applicator surface is curved inwardly.

This has the advantage that the tissue is at least partially. sucked into the cavity thus formed. Depending on the suction effect, the tissue however can also be drawn into the cavity such that the body surface touches the applicator surface. A further advantage follows, particularly for use of the present apparatus for disintegration of soft surface tissue, that the soft tissue near the surface, i.e. especially the epidermis, dermis and fat tissue, can be sucked into the cavity, while the adjacent muscle tissue is less likely to follow due to its higher stability.

A further advantage of the inward curvature of the applicator surface is that the curved applicator surface can cause a focusing of the ultrasound based on its geometry. Another advantage is that the tissue surface, i.e. The surface skin and also the possible tissue transition surface, is normally larger in the sucked in condition than in the normal condition, so that the sound intensity and the undesired heating is reduced.

In a first preferred embodiment, the applicator surface has an approximately radial symmetric spherical cup shape.

A focusing or concentration of the ultrasound into a small volume of body tissue can be achieved with this configuration. By sucking the tissue into the applicator, the focus has a well defined position in the tissue at a well defined distance from body surface.

In a second preferred embodiment, the applicator surface has an approximately cylindric symmetric shape with an approximately U-shaped cross-section.

With this configuration, the ultrasound introduced into the tissue can be focused over the length of the applicator along a line. This has the advantage that a larger and longer surface of the tissue can be treated at the same time. Sucking in the tissue guarantees that the focus of the ultrasound is well defined along a line in the tissue over the length of the applicator.

In an alternative embodiment, the applicator surface is plane. Even with a flat surface, a depth control in the ultrasound therapy is guaranteed in conjunction with the suction apparatus. A focusing of the ultrasound using a planar or flat applicator surface can be achieved in that a phase controlled array of sound transmitters is employed.

In a further preferred embodiment of the present invention, the ultrasound generation unit comprises one or more electrically excitable transducer elements disposed in the applicator surface.

With this feature, the depth control in ultrasound therapy in conjunction with the body surface being drawn onto the applicator surface can be further improved, because the focus of the ultrasound in the body can be fixed with respect to distance by the sucking of the body tissue onto the transducer element. The coupling of the ultrasound into the body tissue is also improved. The transducer elements can be ultrasound transducers in the form of piezo-ceramic elements which generate ultrasound with the power density and frequency required for therapeutic purposes. When using several transducers, correspondingly distributed in the applicator surface, a geometric focusing of the ultrasound can be easily achieved when using a curved configuration of the applicator surface. A slight defocusing can also be achieved with a corresponding arrangement of the transducers or by a corresponding geometric shape of the applicator surface, which then enlarges the effective region of treatment and at the same time avoids overheating of the tissue.

Preferably, the transducer elements are excited with different frequencies and/or different phases.

This has the advantage that the position and extension of the focal region can be adjusted by driving the individual transducers with different frequencies and/or different phases instead of a geometric-electronic adjustment.

In a further embodiment of the present invention, the applicator is combined with a suction and irrigation apparatus for a fluid, which can be brought between the applicator surface and body surface and drawn off again.

Introducing a fluid between the applicator surface and the body surface during ultrasound therapy has the advantage that the body surface is cooled by the fluid. When focusing the ultrasound in the tissue to be treated, the ultrasound passing through the body surface causes a slight heating of the skin surface. This heating can be avoided by the fluid. Further, the introduced fluid has the advantage that it acts as a coupling medium between the applicator surface and the body surface and the ultrasound coupling into the body is improved.

Preferably, a suction channel for the fluid is provided which opens into the applicator surface in a center thereof.

The fluid can then be withdrawn centrally in the coupling region. On the other hand, this suction channel, when interrupting or throttling fluid flow into the region between the applicator surface and the body surface, can be used for sucking the body surface onto the applicator surface, whereby one channel can be saved.

It is also preferred that at least one inlet channel opens at the periphery of the applicator into a region between the applicator surface and the body surface.

This inlet channel can also have an annular configuration.

In conjunction with sucking off at a central region of the applicator surface, this feature has the advantage that fluid introduced from the side edges into the coupling region between the applicator surface and the body surface is well distributed in the coupling region.

In a further preferred embodiment of the present invention, the applicator comprises at its edge periphery a sealing, which forms a seal with the body surface.

On the one hand, this has the advantage that the suction effect when drawing in the body tissue is improved and on the other hand that fluid is securely held in the region between the applicator surface and the body surface. The sealing can comprise a seal strip provided along the circumference of the applicator surface.

In a further preferred embodiment, the depth of focus of the ultrasound in the body tissue is adjustable.

The depth control in a ultrasound therapy can be further improved and the thickness of the tissue layer to be treated can be accounted for. A focal depth corresponding to about half the thickness of the fat tissue layer appears to be favorable. A further advantage results from the adjustability in that one can avoid damage to the muscle tissue below the fat tissue if the penetration depth of ultrasound is too large.

In a further preferred embodiment, the distance between the one or more transducer elements and the body surface is adjustable.

Since the body's surface substantially lies on the applicator surface due to the suction, or is in the direct vicinity, this feature provides the possibility of adjusting the depth of ultrasound focus in the body tissue.

Preferably, a spacer can be attached to the applicator. The spacer represents a simple possibility of altering the penetration depth of ultrasound into the body tissue. Furthermore, the curved chamber or cavity of the applicator can be effectively enlarged by the spacer, so that more tissue can be drawn into the cavity. With a planar applicator surface, a suction chamber can even be formed by using a spacer. As a further advantage, the spacer can simultaneously function as the mentioned sealing with respect to the body surface.

In a further preferred embodiment, the distance between the focus and the applicator surface is within a range of 5 and 40 mm.

With this focal distance from the applicator surface, the entire thickness of the soft tissue near the surface (epidermis, dermis, fat tissue) can be treated in advantageous manner.

In a further embodiment, the applicator comprises at least one ultrasound receiver element, which receives reflected ultrasound and converts same into an electrical signal, which is fed to an evaluation unit.

Due to the differing sound speed in fat tissue and muscle tissue, a partial reflection takes place at the transition layer between the soft tissue near the surface and the muscle tissue. This reflected sound can be received by the receiver element provided on the applicator. The distance between the fat/muscle transition layer and the body surface can then be determined from the reflected ultrasound and with this the thickness of the soft tissue layer close to the surface.

The determination of the position of this transition layer with respect to the body surface has the advantage that the depth control carried out in ultrasound therapy with the present apparatus can be further improved. By determining the depth of the transition between fat tissue and muscle tissue, the power or power density and also the focal depth of ultrasound in the tissue can be adjusted, namely such that no cell destruction occurs in the muscle tissue.

The ultrasound generation apparatus preferably includes at least one transducer element for generating ultrasound in the diagnostic power and frequency range in pulse-echo mode operation.

This can also be the mentioned ultrasound receiver element. While the reflected sound in therapeutic power and frequency range can be used to determine the depth of the soft tissue layer to be treated, the ultrasound in diagnostic power and frequency range, i.e. a relatively high frequency (>1 MHz) and lower power, is more strongly reflected at the tissue transition surface than sound in the therapeutic frequency range and therefore allows a higher resolution. With this, the opportunity is provided to control ultrasound therapy by monitoring the ultrasound, without the need for an additional ultrasound display device.

Pulse-echo operation means that the excitation of the transducer is pulsed such that sound pulses are emitted, where the transducer in the intermediate pauses acts as a receiver element for receiving reflected sound pulses. With this mode of operation, the advantage is achieved that only one transducer is sufficient for sending and receiving ultrasound to obtain a "one dimensional" ultrasound image (A-image).

In a further preferred embodiment, the applicator surface has at least one temperature sensor element arranged thereon.

The temperature sensor, or a thermal-electric element, can measure the temperature on the body surface. The control of the ultrasound treatment is further improved in that the power of the ultrasound can be correspondingly adapted if a corresponding temperature increase is found at the body surface, i.e. The skin. In addition, if a temperature increase is determined as described above, a fluid can be introduced in the coupling region between the body surface and the applicator surface to cool the body surface.

In a further preferred embodiment, the applicator comprises at least one puncture channel.

This has the advantage that disintegrated soft tissue, optionally under ultrasound image control, can be removed or sucked out with a puncture needle introduced through the puncture channel.

It is also preferred that the applicator be provided with at least one electrode on its surface side for measuring the transition resistance between the applicator and the skin surface.

In conjunction with a suitable electric source, the transition resistance between the applicator and the skin surface can be measured locally with the electrode. If several electrodes are provided, the transition resistances between individual regions of the applicator and the corresponding regions of the skin surface can be locally measured, whereby regions of the skin can be found where the contact with the applicator is not optimal. In such a case, the suction action can be increased to achieve a uniform suction of the skin surface and the underlying soft tissue. The ultrasound power coupled into this region of the skin surface can also be reduced or for example a warning signal can also be initiated to recommend or to require a repositioning of the applicator. Thus local overheating of the skin can be avoided. The depth control of the present apparatus is also improved in this embodiment. It is advantageous to provide a plurality of electrodes between the transducer elements, so that local measurements of the transition resistance are possible over the entire therapeutic region of the applicator. The reference electrode necessary for the measurement is preferably provided at the edge of the applicator, for example at the circumferential edge of the applicator, however, it can be directly attached to the patient.

Naturally, the apparatus of the present invention can be employed in miniaturized form for therapy, in particular for endoscopic use.

Further advantages of the invention will become apparent from the following description in conjunction with the appended drawings.

It will be understood that the above-mentioned and following features to be discussed are not limited to the given combinations but apply to other combinations or taken alone without departing from the scope of the present invention.

Embodiments of the invention are illustrated in the drawings and will be discussed in more detail below.

DETAILED DESCRIPTION OF PREFERRED EMBODIMENTS

Figure 1:
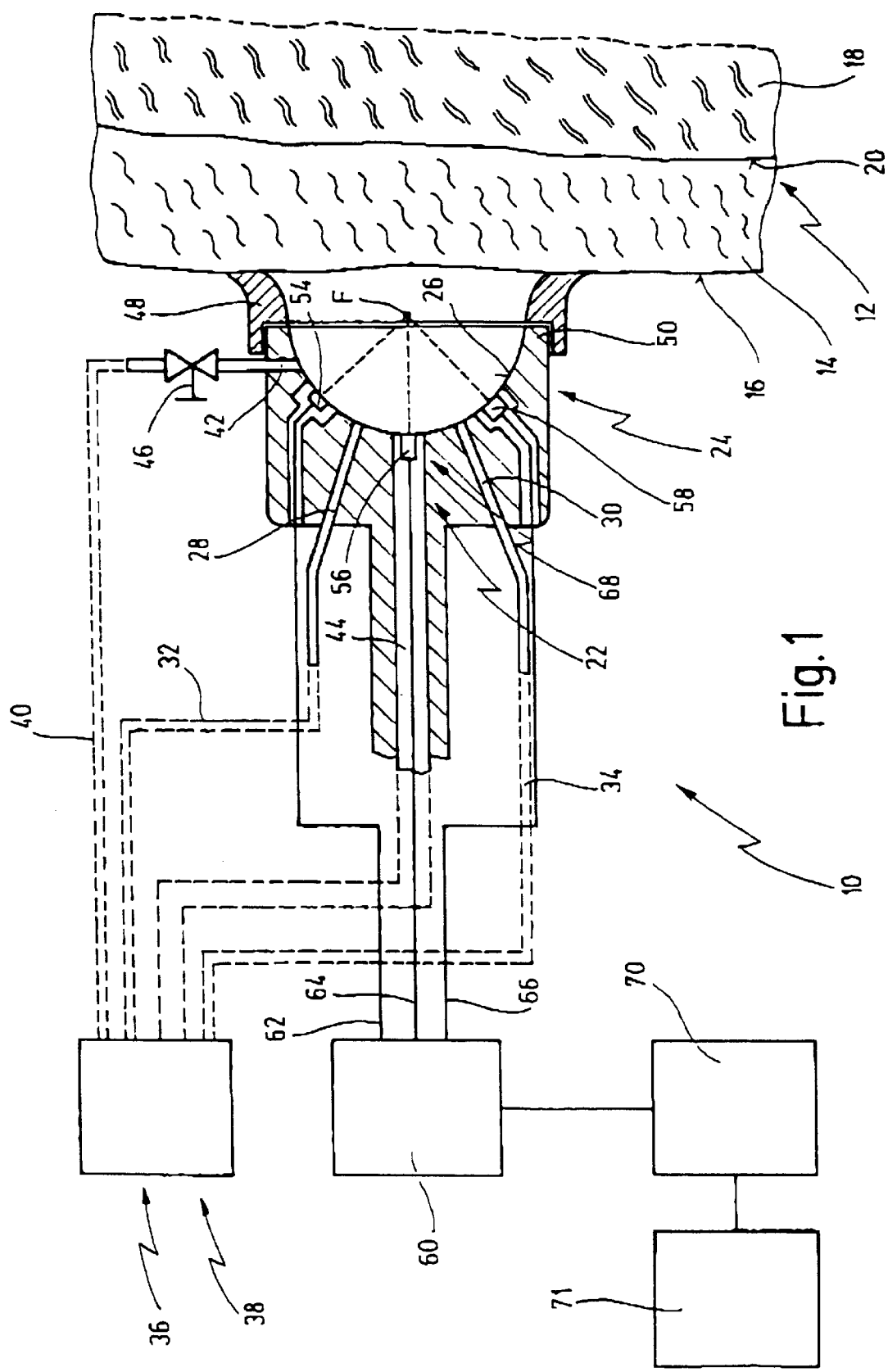
FIG. 1 shows a schematic view partially in cross-section of an apparatus for treating body tissue.

FIG. 1 illustrates an apparatus generally designated with the numeral 10 for treatment of body tissue 12 by means of ultrasound. Body tissue 12 to be treated is a soft tissue 14 near the surface, which includes the epidermis, dermis and fat tissue layers. These lie between body surface 16, i.e. The skin surface and muscle tissue 18 lying adjacent to soft tissue 14. A tissue transition 20 is shown for illustration in FIG. 1 between soft tissue 14 near the surface and muscle tissue 18.

Apparatus 10 comprises an ultrasound generation unit 22 and an applicator 24. The ultrasound is coupled from the outside through body surface 16 into underlying body tissue 12 by means of applicator 24.

Figure 2:
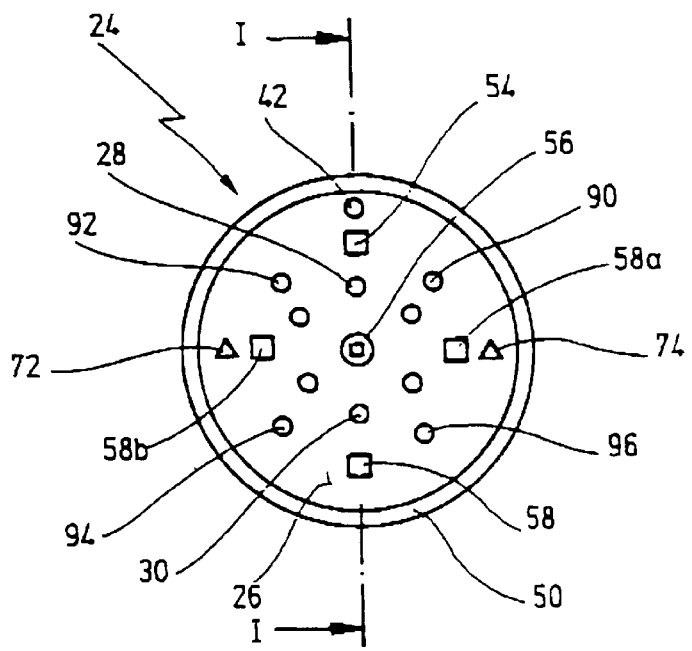
FIG. 2 shows a front view of an applicator of the apparatus of FIG. 1.

An applicator surface 26, which faces body surface 16, is formed with an inward curvature. The applicator surface 26 as illustrated in the embodiments of FIGS. 1 and 2 has an approximately radially symmetrical cup-like shape.

According to the present invention, apparatus 10 comprises a suction apparatus for sucking body surface 16 onto applicator 24 as will be described below. Suction channels 28 and 30 are formed in applicator 24, which join into applicator surface 26. In the embodiment of FIGS. 1 and 2, a total of six suction channels 28, 30 open into applicator surface 26 and are distributed in radially symmetrical manner. Suction channels 28, 30 communicate via connection lines 32, 34 with a suction device 36. Suction device 36 is adapted to apply a vacuum pressure to suction channels 28, 30.

Instead of external suction device 36 and suction channels 28, 30, applicator 24 can be provided in the form of a suction cup. A corresponding lip structure can then be provided at the edge of applicator surface 26, which is both flexible and elastic to be able to act as a suction cup. One or more suction cups can also be provided on applicator surface 26, by which body surface 16 can be drawn onto applicator surface 26.

A suction and irrigation apparatus 38 for a fluid is also integrated into suction device 36. The fluid can be introduced into the region between body surface 16 and applicator surface 26 via a connection line 40 and an inlet channel 42, which joins into applicator surface 26 at an edge of the applicator. The fluid is then withdrawn by means of a suction channel 44 which joins to the central portion of applicator surface 26.

Means 46 for closing off or throttling the fluid flow in inlet channel 42 are provided in connection line 40 between suction and irrigation apparatus 38. Means 46 can be a cut-off valve or a regulator valve for adjusting the vacuum pressure in the space between applicator surface 26 and body surface 16.

A spacer 48 can be secured to edge 50 of applicator 24 between body surface 16 and applicator 24. Spacer 48 is preferably a collar made of elastic material. Spacer 48 at the same time serves to seal applicator 24 with respect to body surface 16. Without spacer 48, a sealing of applicator 24 against the body surface can be achieved by configuring the edge 50 of applicator 24 to be elastic or by applying a sealing material on body surface 16 in the area of edge 50. Several spacers 48 for different spacings can be provided for applicator 24.

Ultrasound generation unit 22 comprises a plurality of transducer elements 54, 56, 58, 58a and 58b, which are preferably arranged symmetrically. In the embodiment of FIGS. 1 and 2, a total of five transducers 54, 56, 58, 58a, 58b is provided. Transducers 54, 56, 58, 58a, 58b are electrically excitable ultrasound transducers, for example piezo-ceramic elements. A control unit 60 is provided for driving transducers 54, 56, 58, 58a, 58b, which is connected to the transducers via electrical lines 62, 64 and 66. Transducer elements 54, 56, 58, 58a, 58b are arranged in applicator surface 26. Due to the approximately radially symmetrical cup-like form of applicator surface 26, the ultrasound emitted from transducers 54, 56, 58, 58a, 58b is focused to a narrowly defined focal region F. More than five transducers 54, 56, 58, 58a, 58b can also be provided, which are distributed in applicator surface 26 or substantially cover applicator surface 26, whose emitted ultrasound is concentrated in the focal region F. The focal region F is located at a distance from the vertex of applicator surface 26 in the range of 5 to 40 mm.

Transducers 54, 56, 58, 58a, 58b are driven by control unit 60 in pulsed or continuous mode depending on whether body tissue 12 is to be treated with a pulsed or continuous ultrasound wave field. It is also possible to drive transducers 54, 56, 58, 58a, 58b with different phases or different frequencies. For example, transducer 54 can be driven at twice the frequency of transducer 58. It is also possible to alter the position and the extension of the focal region F by a corresponding driving program of transducers 54, 56, 58, 58a, 58b via control unit 60.

Further, an ultrasound receiver element 68 is provided in applicator surface 26, which can convert the reflected ultrasound into electrical signals and supply them to an evaluator unit 70 in which the received signals are evaluated. The reflected ultrasound waves include those reflected on the transition from body surface 16, i.e. The skin surface, to soft tissue 14 and those reflected on tissue transition surface 20 between soft tissue 14 and muscle tissue 18. The distance from transition surface 20 to body surface 16 can be determined from the reflected ultrasound signals. Based on the obtained results, the position of the focal region F can then be adjusted as desired.

Instead of providing a receiver element 68 in the applicator surface, it is also possible to make use of transducer 56 located centrally in applicator surface 26 for determining the position of tissue transition layer 20. In this case, transducer 56 is set to emit ultrasound in the diagnostic power range, where transducer 56 then receives reflected ultrasound in the intervals between pulses and converts the ultrasound into an electrical signal. The signal is supplied to evaluator unit 70 via control unit 60. Evaluator unit 70 also has an ultrasound display unit 71 associated therewith.

Furthermore, temperature sensing elements 72, 74 are arranged in applicator 24. Temperature sensors 72, 74, for example thermoelectric elements, are arranged in the edge region of applicator surface 26. The temperature of body surface 16 during treatment of soft tissue 14 can be monitored with temperature sensors 72, 74. Temperature sensors 72, 74 can be connected to control unit 60 or evaluator unit 70 by means of connecting lines (not shown).

Figure 3:
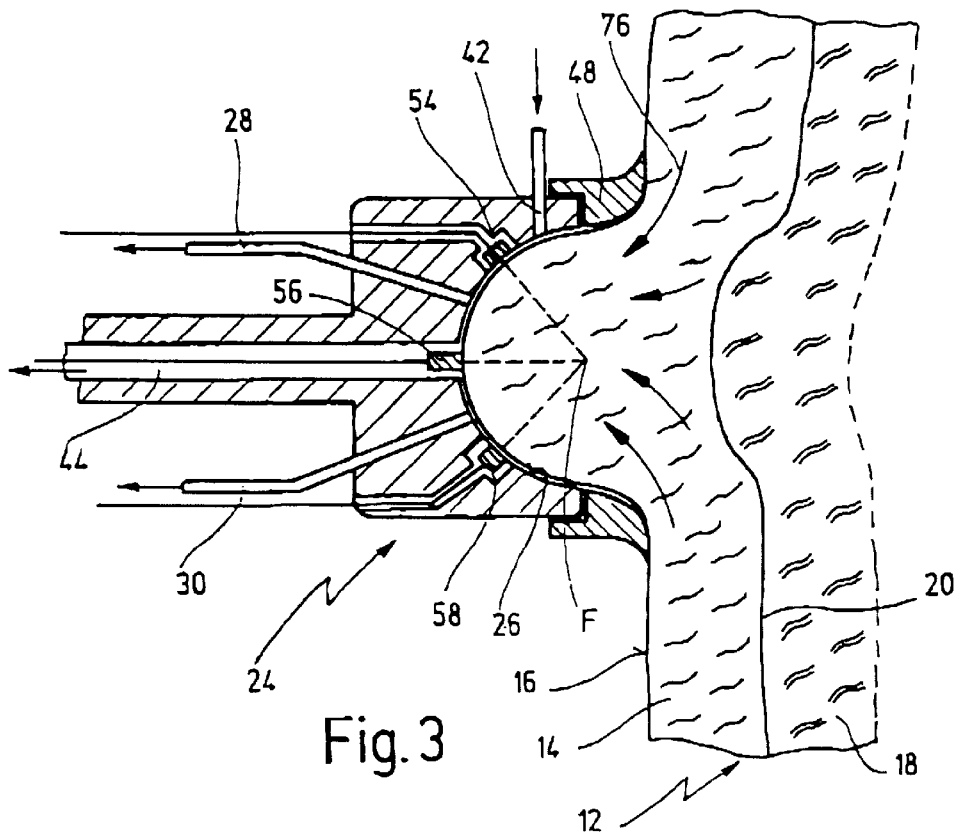
FIG. 3 shows a section of the apparatus of FIG. 1 during the treatment of body tissue.

FIG. 3 illustrates applicator 24 during treatment of body tissue 12. By providing a vacuum pressure in suction lines 28, 30 by suction device 36, surface 16 of the body and therefore soft tissue 14 are sucked into the cavity of applicator 24. Due to the weakness of soft tissue 14, it is more strongly drawn in than harder muscle tissue 14. The arrows 76 illustrate how the soft tissue 14 outside of the circumference of applicator 24 is strongly drawn into the cavity. Ultrasound in the therapeutic power and frequency range is then coupled into soft tissue 14 in focused manner in the focal region F by exciting transducer elements 54, 56, 58, 58a, 58b.

The coupling region between body surface 16 and applicator surface 26 can be filled with fluid before sucking in soft tissue 14 by introducing fluid from suction and irrigation apparatus 38 via inlet channel 42. When Means 46 close connection line 40, the fluid can be withdrawn via suction channel 44 where body surface 16 is sucked into the cavity of applicator 24 at the same time. A fluid layer then remains between body surface 16 and applicator surface 26, which then cools body surface 16, i.e. The skin, during the ultrasound treatment. When means 46 in connection line 40 is not completely closed, a limited fluid flow is also possible, which leads to a particularly effective cooling.

During the soft tissue treatment, the focal region F can be correspondingly adjusted and adapted after determining the position of tissue transition surface 20 as described above. The depth of focus in soft tissue 14 is set to about half the thickness of soft tissue 14 near the surface, i.e. The fat layer. The temperature of body surface 16 is determined during ultrasound treatment by temperature sensing elements 72, 74. Based on the detected temperature, a further adaptation of the ultrasound power can be made. The therapy can be performed with on-line image control by means of ultrasound image display unit 71.

The effects achieved by the therapeutic power level treatment of soft tissue 14 are on the one hand the heating and on the other hand mechanical disintegration resulting from cavitation. The respective desired effects can be achieved by the described adjustability of ultrasound power and frequency and expansion of the focal region F. For treating tumors, the local heating of body tissue 12 is employed by focusing the ultrasound. For disintegration of the soft tissue, the ultrasound effect of cavitation plays a larger role. Cell structures are destroyed by the expansion and bursting of cavitation bubbles.

The threshold values for attaining cavitation lie within a frequency range for the transducers of 750 kHz to 3.5 MHz. A pulsed mode operation of the transducers 54, 56, 58, 58a, 58b favor cavitation more strongly than a continuous operation of transducers 54, 56, 58, 58a, 58b. In addition, pulsed mode operation leads to less heating of the tissue in the focal region F or on body surface 16.

The threshold values for cavitation in the body tissue can be significantly reduced when microbubbles are present in tissue 12 or are introduced into body tissue 12 to be treated. In the case of treating soft tissue 14 near the surface, such as the epidermis, dermis, fat tissue, it is possible to introduce microbubbles without side effects. Ultrasound contrast agents with microbubbles are particularly suited as cavitation promoters, which until now have been used to provide an improved ultrasound representation of vessels.

Figure 4:
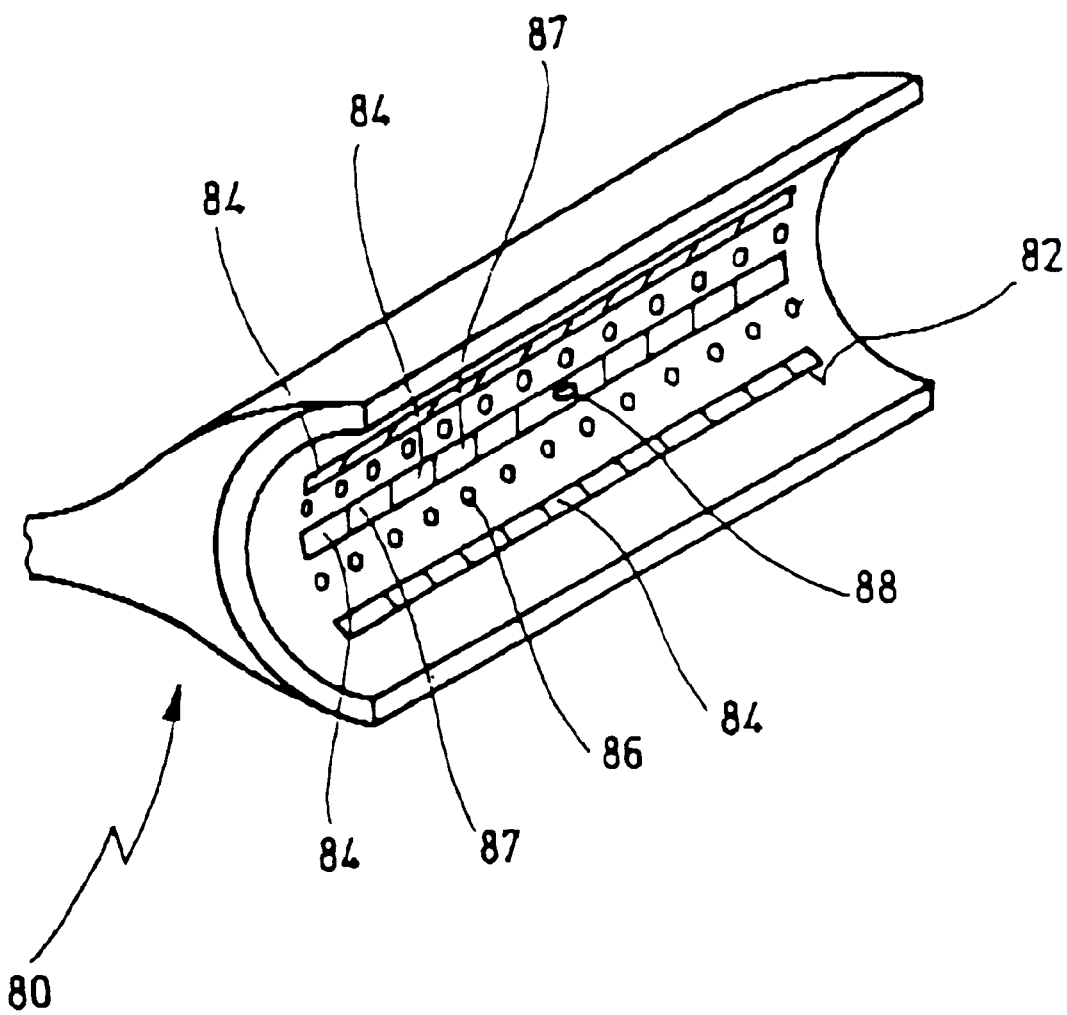
FIG. 4 shows a perspective illustration of a second embodiment of an applicator of the apparatus of FIG. 1.

FIG. 4 illustrates a further embodiment of an applicator 80, which can be employed in apparatus 10 of FIG. 1. Applicator 80 includes an inwardly curved application surface 82. The side portions are not shown for better illustration. Applicator surface 82 is cylindrically symmetrical with an approximate U-shaped cross-section. A plurality of transducer elements 84 in the form of a linear array is arranged in applicator surface 82. With such a configuration of applicator 80, the ultrasound emitted from transducers 84 are not concentrated at a point, but in a focal region along a line. Transducer arrays 84 are preferably driven such that the focus is at a constant distance from the apex of the applicator surface over the entire length of applicator surface 82.

In addition, one or more suction channels 86 join into applicator surface 82 for sucking in body tissue 12, which can also be provided in the form of interconnected open grooves in applicator surface 82.

It will be understood without further explanation that the features discussed in conjunction with applicator 24, for example fluid introduction and withdrawal, can also be employed with applicator 80.

Furthermore, a second array of transducers 87 can be provided for pulse echo mode operation in diagnostic range along the longitudinal direction of applicator 80. An ultrasound B-image can be taken with the second array for controlling the therapy. Transducer elements 84 and 87 can also be arranged alternately along a line in applicator surface 82.

Puncture channels are also provided in applicator 24 of FIG. 1 and applicator 80 of FIG. 4, for example located centrally in the applicator surface, as illustrated with the reference numeral 88 in applicator 80. The puncture channels allow removal of disintegrated soft tissue 14 by means of a needle introduced into the channel under control of the ultrasound image display.

Electrodes 90, 92, 94, 96 are illustrated in applicator surface 26 of applicator 24 shown in FIG. 2, with which a transition resistance between applicator surface 26 and body surface 16 can be measured locally. This is done to control the suction performance and if insufficient contact of the skin with the applicator surface is determined, the suction power can be correspondingly adjusted with the suction device 36. Electrodes 90, 92, 94, 96 are distributed between transducers 54, 56, 58, 58a, 58b and can be provided in a number larger than four to achieve better measurements over the entire surface.

Electrodes 90, 92, 94, 96 are connected to an electrical source, which is not shown here. A reference electrode (not shown) is provided on applicator 24 at its edge, for example, around edge 50 of applicator 24 or is attached directly to the patient.

What we claim is:

1. An apparatus for treating body tissue, superficial soft tissue, with ultrasound, comprising:
   an ultrasonic generation unit;
   an applicator having an applicator surface facing the body surface from which said ultrasound can be irradiated through said body surface into said body tissue,
   wherein a suction apparatus is provided for taking in said body surface against said applicator surface; and
   wherein said applicator surface is curved inwardly.

2. The apparatus of claim 1, wherein said suction apparatus is configured in form of a suction cup.

3. The apparatus of claim 1, wherein said suction apparatus comprises an external suction apparatus combined with said applicator.

4. The apparatus of claim 3, wherein said applicator comprises at least one suction channel opening into said applicator surface and connected to said external suction apparatus.

5. The apparatus of claim 1, wherein said ultrasound can be irradiated by means of said applicator into said body tissue in a focused manner.

6. The apparatus of claim 1, wherein said applicator surface has an approximately radial symmetric spherical U shape.

7. The apparatus of claim 1, wherein said applicator surface is curved inwardly and wherein said applicator surface has an approximately cylindric symmetric shape with an approximately U-shaped cross-section.

8. The apparatus of claim 1, wherein said applicator surface is plane.

9. The apparatus of claim 1, wherein said ultrasonic generation unit comprises at least one electrically excitable transducer element disposed in said applicator surface.

10. The apparatus of claim 9, wherein said transducer elements are excited with different frequencies and/or with different phases.

11. The apparatus of claim 1, wherein said applicator is combined with a suction and irrigation apparatus for a fluid which fluid can be brought between said applicator surface and said body surface and be drawn off again.

12. The apparatus of claim 11, wherein a suction channel for said fluid opens into said applicator surface in a center thereof.

13. The apparatus of claim 1, wherein said applicator is combined with a suction and irrigation apparatus for a fluid which fluid can be brought between said applicator face and said body surface and be drawn off again and wherein at least one inlet channel opens at a periphery of said applicator into a region between said applicator face and said body surface.

14. The apparatus of claim 1, wherein said applicator comprises at the periphery thereof a sealing towards said body surface.

15. The apparatus of claims 1, wherein the depth of focus of said ultrasound in said body tissue is adjustable.

16. The apparatus of claim 1, wherein said ultrasonic generation unit comprises at least one electrically excitable transducer element disposed in said applicator surface and wherein a distance between said at least one transducer element and said body surface is adjustable.

17. The apparatus of claim 1, wherein a spacer attachable to said applicator is provided.

18. The apparatus of claim 1, wherein a distance between the focus of said ultrasound and said applicator surface is within a range of 5 and 40 mm.

19. The apparatus of claim 1, wherein said applicator comprises at least one ultrasonic receiver element receiving reflected ultrasound and converting same into an electric signal, which is fed to an evaluation unit.

20. The apparatus of claim 1, wherein said ultrasonic generation unit comprises at least one transducer element for generating ultrasound in the diagnostic power and frequency range in pulse-echo mode operation.

21. The apparatus of claim 1, wherein at least one temperature registrating element is disposed at said applicator surface.

22. The apparatus of claim 1, wherein said applicator comprises at least one puncture channel.

23. The apparatus of claim 1, wherein at least one electrode for measuring the transition resistance between said applicator face and said body surface is disposed in said applicator at said applicator face thereof.

24. The apparatus of claim 1, wherein said apparatus is configured for the treatment of soft tissue near the inner body surface.

25. The apparatus of claim 24, wherein said apparatus is configured for endoscopic use.

26. A method for treating body tissue, superficial soft tissue, with ultrasound, comprising the steps of:
   providing an ultrasonic generation unit and an applicator having an applicator surface;
   taking in said body surface against said applicator surface;
   irradiating said ultrasound from said applicator surface from outside through a body surface into said body tissue; and
   bringing a fluid between said applicator surface and said body surface.

27. The method of claim 26, wherein said treating of said body tissue consists in disintegrating of said tissue near said body surface.

28. The method of claim 26, wherein said ultrasound is irradiated into said body tissue in a focused manner.

29. The method of claim 28, wherein said ultrasound is focused in said body tissue in a depth within a range of 5 and 40 mm.

30. The method of claim 26, wherein said fluid is permanently brought between said applicator surface and said body surface and drawn off again.

31. The method of claim 26, wherein ultrasound reflected from said body tissue is received and converted into an electric signal, which is fed to an evaluation unit for producing an ultrasound image which is used for controlling the treatment of said body tissue.

32. The method of claim 26, further comprising the step of measuring the temperature of said body surface.

33. The method of claim 26, further comprising the step of measuring the transition resistance between said applicator surface and said body surface.

34. An apparatus for treating body tissue, in particular superficial soft tissue, with ultrasound, comprising:

an ultrasonic generation unit;
an applicator having an applicator surface facing the body surface from which said ultrasound can be irradiated through said body surface into said body tissue,
wherein a suction apparatus is provided for taking in said body surface against said applicator surface; and
wherein said applicator is combined with a suction and irrigation apparatus for a fluid which fluid can be brought between said applicator surface and said body surface and be drawn off again.

35. The apparatus of claim 34, wherein said suction apparatus is configured in form of a suction cup.

36. The apparatus of claim 34, wherein said suction apparatus comprises an external suction apparatus combined with said applicator.

37. The apparatus of claim 36, wherein said applicator comprises at least one suction channel opening into said applicator surface and connected to said external suction apparatus.

38. The apparatus of claim 34, wherein said ultrasound can be irradiated by means of said applicator into said body tissue in a focused manner.

39. The apparatus of claim 34, wherein said applicator surface is curved inwardly.

40. The apparatus of claim 39, wherein said applicator surface has an approximately radial symmetric spherical U shape.

41. The apparatus of claim 34, wherein said applicator surface is curved inwardly and wherein said applicator surface has an approximately cylindric symmetric shape with an approximately U-shaped cross-section.

42. The apparatus of claim 34, wherein said applicator surface is plane.

43. The apparatus of claim 34, wherein said ultrasonic generation unit comprises at least one electrically excitable transducer element disposed in said applicator surface.

44. The apparatus of claim 43, wherein said transducer elements are excited with different frequencies and/or with different phases.

45. The apparatus of claim 34, wherein a suction channel for said fluid opens into said applicator surface in a center thereof.

46. The apparatus of claim 34, wherein said applicator is combined with a suction and irrigation apparatus for a fluid which fluid can be brought between said applicator face and said body surface and be drawn off again and wherein at least one inlet channel opens at a periphery of said applicator into a region between said applicator face and said body surface.

47. The apparatus of claim 34, wherein said applicator comprises at the periphery thereof a sealing towards said body surface.

48. The apparatus of claim 34, wherein the depth of focus of said ultrasound in said body tissue is adjustable.

49. The apparatus of claim 34, wherein said ultrasonic generation unit comprises at least one electrically excitable transducer element disposed in said applicator surface and wherein a distance between said at least one transducer element and said body surface is adjustable.

50. The apparatus of claim 34, wherein a spacer attachable to said applicator is provided.

51. The apparatus of claim 34, wherein a distance between the focus and said applicator surface is within a range of 5 and 40 mm.

52. The apparatus of claim 34, wherein said applicator comprises at least one ultrasonic receiver element receiving reflected ultrasound and converting same into an electric signal, which is fed to an evaluation unit.

53. The apparatus of claim 34, wherein said ultrasonic generation unit comprises at least one transducer element for generating ultrasound in the diagnostic power and frequency range in pulse-echo mode operation.

54. The apparatus of claim 34, wherein at least one temperature registrating element is disposed at said applicator surface.

55. The apparatus of claim 34, wherein said applicator comprises at least one puncture channel.

56. The apparatus of claim 34, wherein at least one electrode for measuring the transition resistance between said applicator face and said body surface is disposed in said applicator at said applicator face thereof.

57. The apparatus of claim 34, wherein it is configured for the treatment of soft tissue near the inner body surface.

58. The apparatus of claim 57, wherein it is configured for endoscopic use.

59. An apparatus for treating body tissue, in particular superficial soft tissue, with ultrasound, comprising:
an ultrasonic generation unit;
an applicator having an applicator surface facing the body surface from which said ultrasound can be irradiated through said body surface into said body tissue,
wherein a suction apparatus is provided for taking in said body surface against said applicator surface; and
wherein said applicator surface is curved inwardly and wherein said applicator surface has an approximately cylindric symmetric shape with an approximately U-shaped cross-section.

60. An apparatus for treating body tissue, in particular superficial soft tissue, with ultrasound, comprising:
an ultrasonic generation unit;
an applicator having an applicator surface facing the body surface from which said ultrasound can be irradiated through said body surface into said body tissue,
wherein a suction apparatus is provided for taking in said body surface against said applicator surface; and
wherein said applicator is combined with a suction and irrigation apparatus for a fluid which fluid can be brought between said applicator face and said body surface and be drawn off again and wherein at least one inlet channel opens at a periphery of said applicator into a region between said applicator face and said body surface.

61. An apparatus for treating body tissue, in particular superficial soft tissue, with ultrasound, comprising:
an ultrasonic generation unit;
an applicator having an applicator surface facing the body surface from which said ultrasound can be irradiated through said body surface into said body tissue,
wherein a suction apparatus is provided for taking in said body surface against said applicator surface; and
wherein a spacer attachable to said applicator is provided.

62. An apparatus for treating body tissue, in particular superficial soft tissue, with ultrasound, comprising:
an ultrasonic generation unit;
an applicator having an applicator surface facing the body surface from which said ultrasound can be irradiated through said body surface into said body tissue,
wherein a suction apparatus is provided for taking in said body surface against said applicator surface; and
wherein said applicator comprises at least one ultrasonic receiver element receiving reflected ultrasound and converting same into an electric signal, which is fed to an evaluation unit.

63. An apparatus for treating body tissue, in particular superficial soft tissue, with ultrasound, comprising:

an ultrasonic generation unit;

an applicator having an applicator surface facing the body surface from which said ultrasound can be irradiated through said body surface into said body tissue, wherein a suction apparatus is provided for taking in said body surface against said applicator surface; and wherein said ultrasonic generation unit comprises at least one transducer element for generating ultrasound in the diagnostic power and frequency range in pulse-echo mode operation.

64. An apparatus for treating body tissue, in particular superficial soft tissue, with ultrasound, comprising:

an ultrasonic generation unit;

an applicator having an applicator surface facing the body surface from which said ultrasound can be irradiated through said body surface into said body tissue, wherein a suction apparatus is provided for taking in said body surface against said applicator surface; and wherein at least one temperature registrating element is disposed at said applicator surface.

65. An apparatus for treating body tissue, in particular superficial soft tissue, with ultrasound, comprising:

an ultrasonic generation unit;

an applicator having an applicator surface facing the body surface from which said ultrasound can be irradiated through said body surface into said body tissue, wherein a suction apparatus is provided for taking in said body surface against said applicator surface; and wherein said applicator comprises at least one puncture channel.

66. An apparatus for treating body tissue, in particular superficial soft tissue, with ultrasound, comprising:

an ultrasonic generation unit;

an applicator having an applicator surface facing the body surface from which said ultrasound can be irradiated through said body surface into said body tissue, wherein a suction apparatus is provided for taking in said body surface against said applicator surface; and wherein at least one electrode for measuring the transition resistance between said applicator face and said body surface is disposed in said applicator at said applicator face thereof.

67. A method for treating body tissue, in particular superficial soft tissue, with ultrasound, comprising the steps of:

providing an ultrasonic generation unit and an applicator having an applicator surface;

taking in said body surface against said applicator surface; and irradiating said ultrasound from said applicator surface from outside through a body surface into said body tissue, wherein said treating of said body tissue consists in disintegrating of said tissue near said body surface.

68. A method for treating body tissue, in particular superficial soft tissue, with ultrasound, comprising the steps of:

providing an ultrasonic generation unit and an applicator having an applicator surface;

taking in said body surface against said applicator surface; and irradiating said ultrasound from said applicator surface from outside through a body surface into said body tissue, wherein ultrasound reflected from said body tissue is received and converted into an electric signal, which is fed to an evaluation unit for producing an ultrasound image which is used for controlling the treatment of said body tissue.

69. A method for treating body tissue, in particular superficial soft tissue, with ultrasound, comprising the steps of:

providing an ultrasonic generation unit and an applicator having an applicator surface;

taking in said body surface against said applicator surface;

irradiating said ultrasound from said applicator surface from outside through a body surface into said body tissue; and measuring the temperature of said body surface.

70. A method for treating body tissue, in particular superficial soft tissue, with ultrasound, comprising the steps of:

providing an ultrasonic generation unit and an applicator having an applicator surface;

taking in said body surface against said applicator surface;

irradiating said ultrasound from said applicator surface from outside through a body surface into said body tissue; and measuring the transition resistance between said applicator surface and said body surface.

* * * * *